(12) United States Patent
Konno et al.

(10) Patent No.: US 10,070,776 B2
(45) Date of Patent: Sep. 11, 2018

(54) ENDOSCOPE DEVICE WITH LENS MOVING UNIT FOR CHANGING OBSERVATION DEPTH BASED ON CAPTURED IMAGES

(71) Applicant: OLYMPUS CORPORATION, Tokyo (JP)

(72) Inventors: Mitsujiro Konno, Tokyo (JP); Akikazu Yachi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/137,576

(22) Filed: Apr. 25, 2016

(65) Prior Publication Data
US 2016/0235281 A1 Aug. 18, 2016

Related U.S. Application Data

(63) Continuation of application No. PCT/JP2014/083035, filed on Dec. 12, 2014.

(30) Foreign Application Priority Data

Dec. 16, 2013 (JP) .................................. 2013-259202

(51) Int. Cl.
*A61B 1/06* (2006.01)
*A61B 1/04* (2006.01)
(Continued)

(52) U.S. Cl.
CPC ...... *A61B 1/00188* (2013.01); *A61B 1/00096* (2013.01); *A61B 1/00133* (2013.01);
(Continued)

(58) Field of Classification Search
CPC ........... A61B 1/06; A61B 1/0638; A61B 1/00; A61B 1/04; A61B 1/07; A61B 1/00117;
(Continued)

(56) References Cited

U.S. PATENT DOCUMENTS 4,570,185 A * 2/1986 Arai .................. H04N 5/23212
348/345
4,781,448 A * 11/1988 Chatenever .............. A61B 1/04
359/701
(Continued)

FOREIGN PATENT DOCUMENTS

EP 2904961 8/2015
JP 09-80323 3/1997
(Continued)

OTHER PUBLICATIONS

International Search Report, dated Mar. 17, 2015, issued in corresponding International Application No. PCT/JP2014/083035.
(Continued)

*Primary Examiner* — John P Leubecker
*Assistant Examiner* — William Chou
(74) *Attorney, Agent, or Firm* — Hunton Andrews Kurth LLP

(57) ABSTRACT

This endoscope device can simplify the determination of the moving direction of a focusing lens, and can improve the accuracy of auto focusing. The endoscope has the following elements: an optical system having a focusing lens; a lens moving unit which moves the focusing lens along an optical axis thereof; an image capturing unit which obtains an optical image of an object from the optical system as a plurality of images each of which has a different focal position from each other; a moving direction determining section which determines whether to change the observation depth on the basis of the plurality of images, and determines a moving direction toward which the focusing lens is to be moved on the bases of the images; and a drive control unit which controls the lens moving unit to move the focusing lens toward a determined moving direction.

5 Claims, 3 Drawing Sheets

(51) Int. Cl.
  *A61B 1/00* (2006.01)
  *G02B 23/26* (2006.01)
  *A61B 1/045* (2006.01)
  *G02B 7/38* (2006.01)
  *G02B 23/24* (2006.01)
  *A61B 5/06* (2006.01)
  *H04N 5/232* (2006.01)
  *A61B 1/05* (2006.01)
  *H04N 5/225* (2006.01)

(52) U.S. Cl.
  CPC ............... *A61B 1/045* (2013.01); *A61B 5/06* (2013.01); *A61B 5/065* (2013.01); *G02B 7/38* (2013.01); *G02B 23/243* (2013.01); *G02B 23/26* (2013.01); *H04N 5/23212* (2013.01); *A61B 1/00006* (2013.01); *A61B 1/04* (2013.01); *A61B 1/05* (2013.01); *H04N 2005/2255* (2013.01)

(58) Field of Classification Search
  CPC ........... A61B 1/00121; A61B 1/00126; A61B 1/00163; A61B 1/00165; A61B 1/00167; A61B 1/00188; A61B 1/0019; G02B 6/38; G02B 6/40
  USPC ....... 600/109, 132, 136, 160, 167, 168, 172, 600/175, 176, 178, 182; 385/54, 55, 100, 385/116, 117; 348/65
  See application file for complete search history.

(56) References Cited

U.S. PATENT DOCUMENTS

| | | | | |
|---|---|---|---|---|
| 4,873,572 | A * | 10/1989 | Miyazaki | A61B 1/00193 348/45 |
| 7,469,160 | B2 * | 12/2008 | Banks | A61B 5/0059 600/123 |
| 2006/0238614 | A1 * | 10/2006 | Konno | A61B 1/00096 348/69 |
| 2007/0156021 | A1 * | 7/2007 | Morse | A61B 1/0019 600/167 |
| 2009/0046196 | A1 * | 2/2009 | Lavrentiev | A61B 1/00188 348/345 |
| 2009/0259101 | A1 * | 10/2009 | Unsai | A61B 1/00096 600/110 |
| 2011/0128640 | A1 | 6/2011 | Koh | |
| 2013/0235174 | A1 | 9/2013 | Namii | |
| 2015/0002646 | A1 | 1/2015 | Namii | |
| 2015/0309284 | A1 | 10/2015 | Kagawa et al. | |
| 2015/0339817 | A1 * | 11/2015 | Kuriyama | G06T 1/0007 348/71 |
| 2017/0245744 | A1 * | 8/2017 | McDowall | A61B 1/051 |

FOREIGN PATENT DOCUMENTS

| | | |
|---|---|---|
| JP | 2002-28126 | 1/2002 |
| JP | 2009-80413 | 4/2009 |
| JP | 4336166 | 9/2009 |
| JP | 2012-95828 | 5/2012 |
| JP | 2013-22262 | 2/2013 |
| JP | 2013-61618 | 4/2013 |
| JP | 2013-101314 | 5/2013 |
| JP | 2013-183836 | 9/2013 |
| JP | 2013-230289 | 11/2013 |
| JP | 2013-230319 | 11/2013 |
| WO | 2013/027459 | 2/2013 |

OTHER PUBLICATIONS

Supplementary European Search Report for Application No. 14871544.4, dated Sep. 4, 2017.

* cited by examiner

ENDOSCOPE DEVICE WITH LENS MOVING UNIT FOR CHANGING OBSERVATION DEPTH BASED ON CAPTURED IMAGES

CROSS-REFERENCE TO RELATED APPLICATIONS

This application is a Continuation Application of International Application No. PCT/JP2014/083035 filed on Dec. 12, 2014, which claims priority to Japanese Application No. 2013-259202 filed on Dec. 16, 2013. The Contents of International Application No. PCT/JP2014/083035 and Japanese application No. 2013-259202 are hereby incorporated herein by reference in its entirety.

TECHNICAL FIELD

The present invention relates to an endoscope device, more particularly to an endoscope device having an auto focusing function.

BACKGROUND ART

The conventional optical devices have adopted a low pixel number imaging element for reducing the size of the device, and can obtain images with sufficiently wide depth of field only by narrowing the aperture stop of the optical system.

Recently, fining pixels of imaging elements achieved a certain progress, and therefore it has become possible to perform more detailed observation and diagnosis, applying the imaging device having a large number of pixels in an endoscope apparatus. In such endoscope devices, when the aperture stop of the optical system is much reduced in order to ensure the depth of field, the quality of the obtained image quality becomes deteriorated due to the diffraction limit. On the other hand, if the aperture stop cannot be narrowed, the depth of field becomes shortened. Thus, endoscope devices, which have an auto focus function to be able to automatically focus within narrow depth of field, have been proposed. For example, Patent Literature 1 discloses an Auto Focusing endoscope which drives the aperture stop and the lens, using brightness information.

CITATION LIST

Patent Literature

{PTL 1} Japanese Unexamined Patent Application, Publication No. 2013-22262

SUMMARY OF INVENTION

An aspect of the present invention is an endoscope device comprising the following elements: an optical system having a focusing lens; a lens moving unit which moves the focusing lens along an optical axis thereof in order to change an observation depth; an image capturing unit which obtains an optical image of an object from the optical system as a plurality of images each of which has a different focal position from each other; a moving direction determining section which determines whether to change the observation depth on the basis of the plurality of images, and determines, when the observation depth is determined to be changed, a moving direction toward which the focusing lens is to be moved on the bases of the images; and a drive control unit which controls the lens moving unit to move the focusing lens toward a determined moving direction.

DESCRIPTION OF EMBODIMENTS

An endoscope device according to an embodiment of the present invention will be described below with reference to the drawings.

Figure 1:
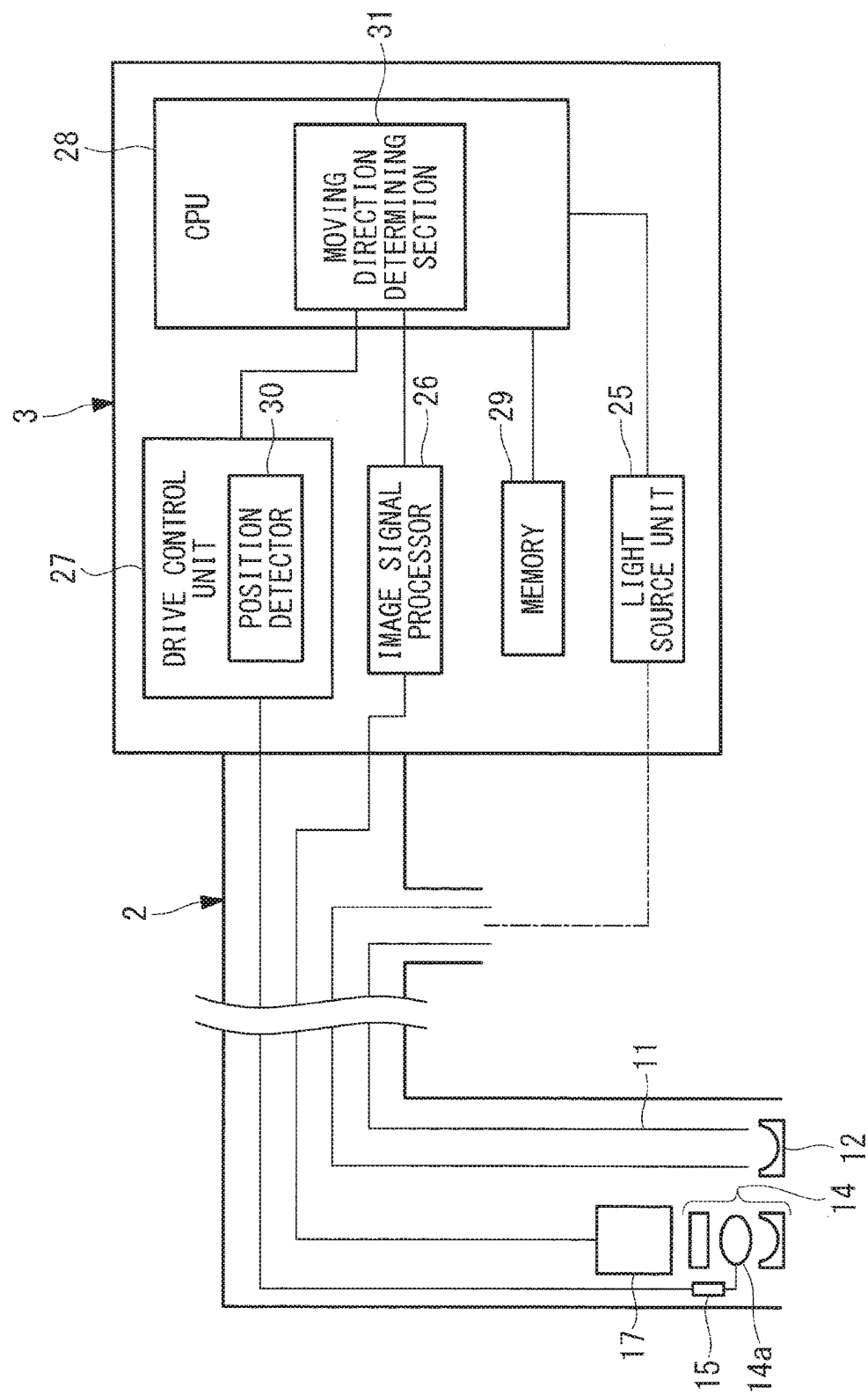
FIG. 1 is a block diagram showing a schematic configuration of an endoscope device according to an embodiment of the present invention.

As shown in FIG. 1, the endoscope device has a slender inserted portion 2 to be inserted into an object, and an endoscope controller 3 which performs various controls for supplying the illumination light to the insertion portion 2, obtaining observation images of the object, and the like, according to operational instructions by an operator.

A light guide 11 for guiding the illumination light is inserted into the inserted portion 2. An illumination lens 12 which emits the illumination light toward the object is provided on the distal end side of the light guide 11, and the proximal end side of the light guide 11 is connected to the light source unit 25, which will be described later, via a cable and connector which are not shown in the drawings. Therefore, the illumination light from the light source unit 25 through the light guide 11 and the illumination lens 12 is irradiated to the object.

Further, an optical system 14, which forms an optical image of the illuminated object, is provided in the insertion portion 2. The optical system 14 has a focusing lens 14a, and can change the observation depth regarding the object by moving the focusing lens 14a in the optical axis direction. This embodiment is explained about a configuration in which the observation depth is changed to a magnified observation and a normal observation. In this embodiment, as shown in FIG. 2, the focusing lens 14a is moved in the optical axis direction by means of an actuator 15, and the focusing lens 14a is able to move within a predetermined range, and thereby the observation mode can be changed to the magnified and normal ones by moving the focusing lens 14a.

The inserted portion 2 is provided with an image capturing unit 17 which obtains optical images of the object, which is formed by the optical system 14, and each of which has a plurality of images with different focal positions. In this embodiment, the following explanation is made about a configuration in which the images of two focal points of a distant point image and a near point image are obtained.

Figure 2:
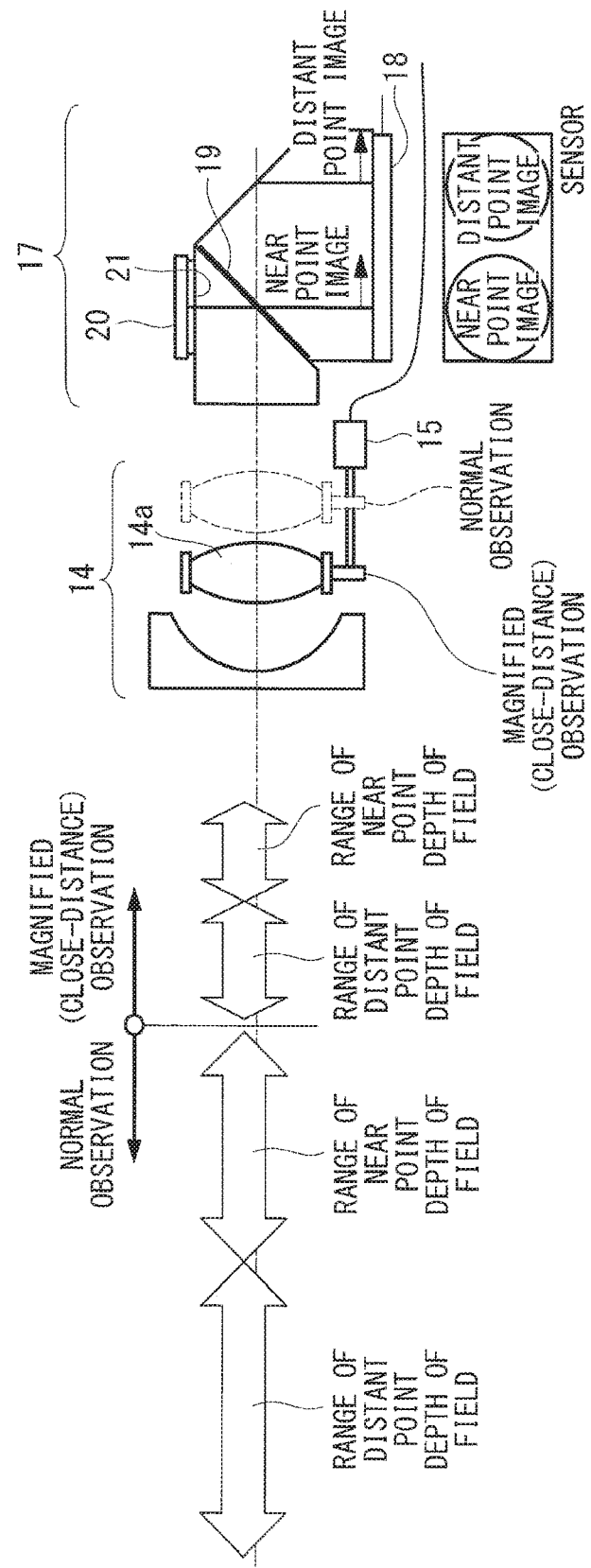
FIG. 2 is an explanatory view showing a structure from an optical system to an imaging unit of the endoscope device according to the embodiment of the present invention.

As shown in FIG. 2, the image capturing unit 17 comprises a polarizing beam splitter 19, mirror 20, and a λ/4 wave plate 21, and thereby the image capturing unit 17 forms two optical images which are the distant point image and the near point image, using the condensed light by the optical system 14. Also, the image capturing unit 17 has an imaging element 18 whose imaging surfaces are located at the image forming positions, and obtains images at the two focal positions of the distant point image and the near point image.

Thus, as shown in FIG. 2, when the focusing lens 14a is positioned on a near point side of the movable range, the image capturing unit 17 can perform a magnified observation, obtaining the near point image and the distant point image in the magnified observation mode. Also, when the focusing lens 14a is positioned on a distant point side of the movable range, it is possible to perform a normal observation, obtaining the near point image and the distant point image in the normal observation mode.

The image capturing unit 17 is connected to an image signal processor 26 of the endoscope controller 3 via cable and a connector which are not shown in the drawings.

The endoscope controller 3 includes the light source unit 25 which emits illumination light, the image processing unit 26 which performs a predetermined signal process on the image obtained by the imaging unit 17, and a drive control unit 27 that performs autofocusing by moving the focus lens by controlling the actuator, and a CPU 28 which controls these units.

The light source unit 25 includes a lamp serving as the light source for generating illumination light, and a light amount adjusting unit which adjusts the amount of the light emitted from the lamp, and the light source unit 25 supplies a required amount of illuminating light to the light guide 11.

The drive control unit 27 controls the actuator 15 to move the focus lens according to the command from the CPU 28. Also, the unit includes a position detector 30 for detecting the position information which indicates the current position of the actuator 15 in the movable range.

The CPU 28 controls the above-described components, and determines whether or not to switch the observation depth based on an image obtained by the image capturing unit 17. The CPU 28 includes a moving direction determining section 31 which determines the moving direction of the focus lens on the basis of said images when it is determined that the switching of the observation depth becomes necessary, and outputs a determined moving direction to the drive control unit 27.

The endoscope controller 3 includes a memory 29 which stores various types of data, such as a threshold value that is required when judging whether switching of the observation mode by the CPU 28 is necessary or not.

The determination of necessity of the switching of the observation depth or the determination of the moving direction is performed based on the plurality of images obtained by the image capturing unit 17, preferably, for example, based on the characteristics of the images, the contrast, the brightness, the frequency component.

Figure 3:
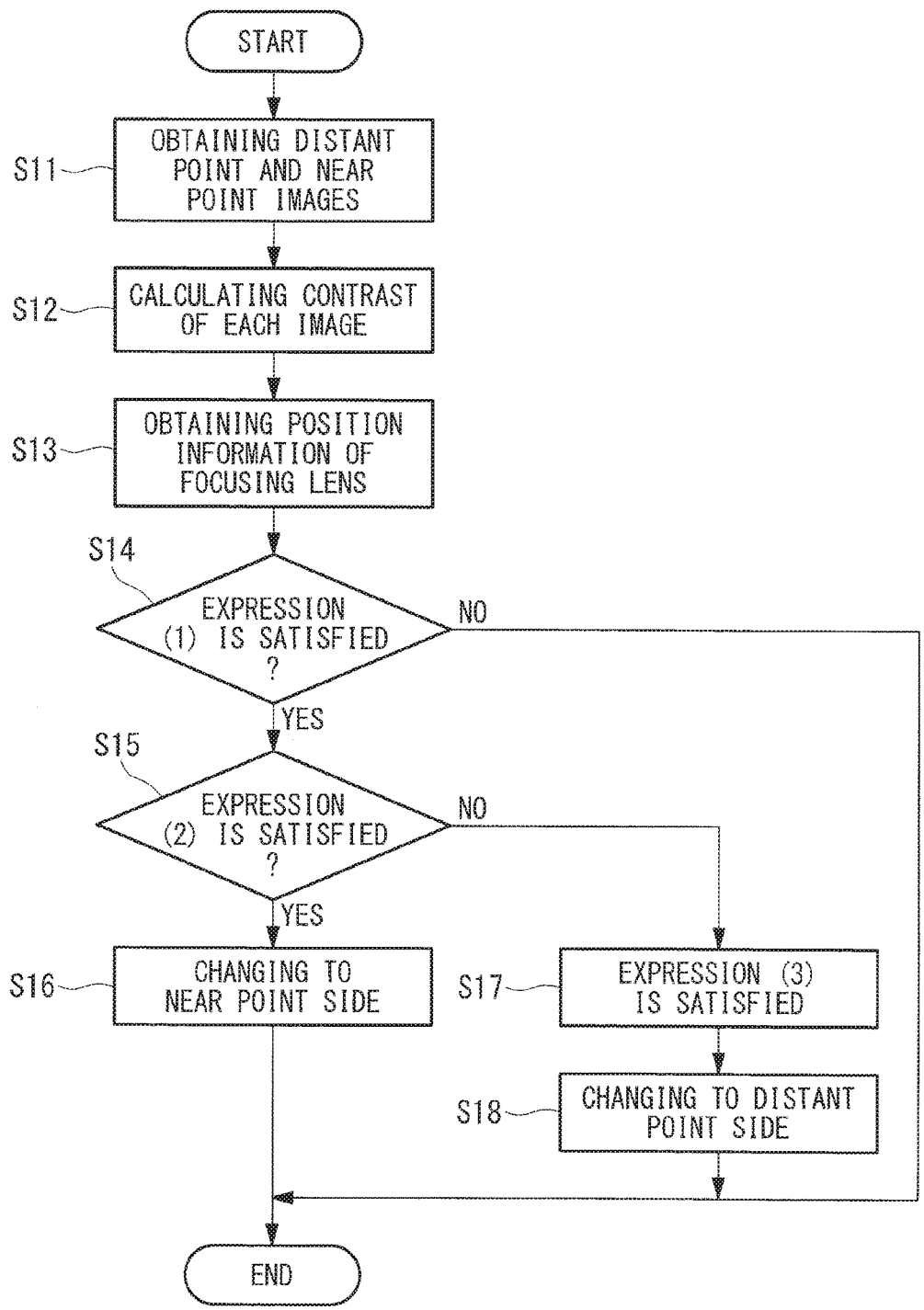
FIG. 3 is a flowchart showing a function of the endoscope device according to the embodiment of the present invention.

The operation of the endoscope device configured in this manner, more particularly, the switching of the observation depth and the determination of the movement direction will be described with reference to the flowchart of FIG. 3.

The following description is made about a configuration in which the contrast of the image is used as an evaluation value for evaluating the image when determining whether the switching of the observation depth is necessary or not.

In the step S11, when the focusing lens 14a is located at an arbitrary position within the movable range, the distant point image and the near point image in the position are captured by the image capturing unit 17, and an image signal derived from the distant point image and the near point image is output to the CPU 28 after a predetermined signal process is carried out. In the next step S12, the CPU 28 calculates the contrasts as an evaluation value for each of the images. That is, the contrasts are calculated so as to include the contrast of the near point image being F1 and as the contrast of the distant point image being F2, respectively.

In the step S13, the CPU 28 obtains, from the position detector 30, position information indicating the position of the focusing lens 14a within the movable range at the time of obtaining the image in the step S11. In the step S14, threshold values Th1 and Th2 which correspond to the obtained position information of the focusing lens 14a are read out from the memory 29 as a first process. Th1 and Th2 are threshold values predetermined in accordance with the position of the focusing lens 14a when the distant point image and the near point image are obtained, and the threshold values are stored in the memory 29. Then, the CPU 28 determines whether the switching of the observation depth is necessary in order to satisfy the following conditional expression (1).

$$(F1 \leq Th1) \cap (F2 \leq Th2) \tag{1}$$

In the step S14, when the above expression (1) is not satisfied, the movement of the focusing lens 14a is determined to be unnecessary, and the CPU 28 does not output any signal to the drive control unit 27.

On the other hand, when the above expression (1) is satisfied, the process proceeds to the step S15, and the moving direction to which the focusing lens 14a is to be moved is determined for the switching of the observation depth.

The moving direction of the focusing lens 14a is determined as follows. More specifically, when the following conditional expression (2) is satisfied, the process proceeds to the step S16 and determines that the moving direction of the focusing lens is the near point side.

$$F1 > F2 \tag{2}$$

That is, when the expression (2) is satisfied, the moving direction determining section 31 outputs a signal to the drive control unit 27 so that the focusing lens 14 is moved toward the near point side. When the focus lens 14a is positioned at the normal observation position, the signal for moving the lens to the magnified observation position is output from the CPU 28 to the drive control unit 27. When the focusing lens 14a is positioned at the nearest point of the movable range, even if an additional signal for moving the lens toward the near point side is output, this does not cause any problem since the focusing lens 14a does not move beyond the movable range. On the other hand, it is possible not to output the signal for moving the lens toward the near point side by detecting the current position of the focusing lens 14a.

On the other hand, when the conditional expression (2) is not satisfied, the process proceeds to the step S17. When the conditional expression (2) is not satisfied, that is, when the conditional expression (3) is satisfied, the process proceeds to the step S18 and the process determines that the moving direction of the focus lens is the distant point side.

$$F1 \leq F2 \tag{3}$$

That is, when the expression (3) is satisfied, the moving direction determining section 31 outputs a signal to the drive control unit 27 so that the focusing lens 14a is moved toward the distant point side. That is, when the focusing lens 14a is positioned in the magnified observation position, the CPU 28 outputs a signal, which is for moving the lens to the normal observation position, to the drive control unit 27.

When the focusing lens 14a is positioned at the most distant point of the movable range, even if an additional signal for moving the lens toward the distant point side is output, this does not cause any problem since the focusing lens 14a does not move beyond the movable range. On the other hand, it is possible not to output the signal for moving the lens toward the distant point side by detecting the current position of the focusing lens 14a.

As described above, according to this embodiment, when the focusing lens 14a is at any position on the optical axis, the optical images from the optical system 14 are respectively obtained as a plurality of images with different focal positions, and the determination as to whether or not to change the observation depth based on these images is performed. That is, since the device determines whether or not to switch the observation depth prior to the focusing, it becomes possible to prevent unnecessary operations of moving the focusing lens 14a when the device is in the in-focus state, and also it becomes possible to stabilize the operation of the endoscope device.

On the other hand, since the moving direction of the focusing lens 14a is determined when the device determines that the switching of the observation depth is necessary, it is possible to prevent unnecessary operations of the focusing lens 14a, and it is also possible to achieve accurate focusing even in the case in which the depth of field is narrow and therefore the focusing is difficult.

Further, the determinations as to whether to switch the observation depth and as to the moving direction of the focusing lens 14 are performed based on a plurality of images each of which has a different focal position from each other. Thus, the characteristics of the plurality of images, that is, the contrast, the brightness, the frequency component thereof, and the like can be utilized, and therefore, it is possible to perform an accurate focusing. Thus, it is possible to improve the accuracy of auto focusing in an endoscope device in which the observation depth is changeable and fine observation images can be obtained.

The inventors have arrived at the following aspects of the invention.

An aspect of the present invention is an endoscope device comprising the following elements: an optical system having a focusing lens; a lens moving unit which moves the focusing lens along an optical axis thereof in order to change an observation depth; an image capturing unit which obtains an optical image of an object from the optical system as a plurality of images each of which has a different focal position from each other; a moving direction determining section which determines whether to change the observation depth on the basis of the plurality of images, and determines, when the observation depth is determined to be changed, a moving direction toward which the focusing lens is to be moved on the bases of the images; and a drive control unit which controls the lens moving unit to move the focusing lens toward a determined moving direction.

According to this aspect, the observation is performed, appropriately changing the observation depth by moving the focusing lens of the optical system along the optical axis by means of the lens moving unit. In this process, when the focusing lens is located at an arbitrary position on the optical axis, that is, when it is in an arbitrary observation depth, the image capturing unit captures an optical image from the optical system as a plurality of images each of which has a different focal position from each other, and moving direction determining section determines whether or not to change the observation depth on the basis of these images. Since the moving direction determining section determines whether or not to change the observation depth prior to the focusing, it becomes possible to prevent unnecessary operations of moving the focusing lens 14a when the device is in the in-focus state, and also it becomes possible to stabilize the operation of the endoscope device.

On the other hand, since the moving direction of the focusing lens is determined by the moving direction determining section when the device determines that the switching of the observation depth is necessary, it is possible to prevent unnecessary operations of the focusing lens, and it is also possible to achieve accurate focusing even in the case in which the depth of field is narrow and therefore the focusing is difficult.

Further, the determinations as to whether to switch the observation depth and as to the moving direction of the focusing lens are performed based on a plurality of images each of which has a different focal position from each other. Thus, the characteristics of the plurality of images, that is, the contrast, the brightness, the frequency component thereof, and the like can be utilized, and therefore, it is possible to perform an accurate focusing. Thus, it is possible to improve the accuracy of auto focusing in an endoscope device in which the observation depth is changeable and fine observation images can be obtained.

In the above-described aspect, it is preferable that the device further comprises a position detector for detecting position information which indicates a position of the focusing lens at the time of obtaining the plurality of images, wherein the moving direction determining section calculates contrasts of the plurality of images, respectively, and determines that the observation depth is to be changed when the calculated contrasts are smaller than a threshold value which is predetermined in relation to the position information.

Since the characteristics of the images defer due to the position of the focusing lens, the device obtains the position information which indicates the position of the focusing lens at the time of obtaining the image. Also, the device calculates the contrast which indicates a characteristic of the image, and then determines whether or not to change the observation depth by comparing the contrast with the threshold value corresponding to the position information. Therefore, it is possible to accurately determine whether or not to change the observation depth.

In the above-described aspect, it is preferable that the moving direction determining section determines the moving direction of the focusing lens so that the observation depth is changed toward a direction by which the observation depth is moved from a focal position of an obtained image corresponding to a minimum contrast of the calculated contrasts to a focal position of an obtained image corresponding to a maximum contrast of the calculated contrasts.

By employing the aforementioned configuration, especially when a plurality of observation depths between the magnified observation and the normal observation can be chosen, it is possible to prevent unnecessary operations of the focusing lens, and it is also possible to achieve accurate focusing even in the case in which the depth of field is narrow and therefore the focusing is difficult.

In the above-described aspect, it is preferable that the image capturing unit captures a near point image whose focal position is at a near point and a distant point image whose focal position is at a distant point, and that the moving direction determining section calculates a contrast F1 of the near point image and a contrast F2 of the distant point image, and determines that the observation depth is to be changed when the following conditional expression (1) is satisfied.

$$(F1 \leq Th1) \cap (F2 \leq Th2) \tag{1}$$

In the expression, the near point threshold Th1 and the distant point threshold Th2 are predetermined so as to correspond to the position information of the focusing lens at the time of obtaining the near point image and the distant point image.

By employing the aforementioned configuration, the determination as to whether or not to change the observation depth can be done precisely, and therefore it becomes possible to improve the accuracy of the auto focusing.

In the above-described aspect, it is preferable that the moving direction determining section determines that the moving direction is a direction toward the near point when the following conditional expression (2) is satisfied, and that the moving direction is a direction toward the distant point when the following conditional expression (3) is satisfied.

$$F1 > F2 \tag{2}$$

$$F1 \leq F2 \tag{3}$$

By employing the aforementioned configuration, the determination as to whether or not to change the observation depth can be simplified, therefore it becomes possible to further improve the accuracy of the auto focusing.

The aforementioned aspects affords an advantage of improving the accuracy of the auto focusing in an endoscope device in which the observation depth can be changed and accurate observation images can be obtained.

REFERENCE SIGNS LIST 2 inserted portion
3 endoscope controller
11 light guide
12 illumination lens
14 optical system
14a focusing lens
15 actuator
17 image capturing unit
18 imaging element
19 polarizing beam splitter
20 mirror
21 λ/4 wave plate
25 light source unit
26 image signal processor
27 drive control unit
28 CPU
29 memory
30 position detector
31 moving direction determining section

The invention claimed is:

1. An endoscope device comprising:
an optical system having a focusing lens;
a lens moving unit which moves the focusing lens along an optical axis thereof in order to change an observation depth when observing an object;
an image capturing unit which simultaneously obtains a plurality of images of the object through the optical system when the focusing lens is located at a position by the lens moving unit, focal positions of the plurality of images being different from each other when the focusing lens is located at the position
a moving direction determining section which determines whether to change the observation depth on the basis of the plurality of images, and determines, when the observation depth is determined to be changed, a moving direction toward which the focusing lens is to be moved on the bases of the images; and
a drive control unit which controls the lens moving unit to move the focusing lens toward a determined moving direction.

2. The endoscope device according to claim 1, further comprising a position detector for detecting position information which indicates a position of the focusing lens at the time of obtaining the plurality of images,
wherein the moving direction determining section calculates contrasts of the plurality of images, respectively, and determines that the observation depth is to be changed when all of the calculated contrasts are smaller than threshold values which are respectively set for the calculated contrasts and which are predetermined in relation to the position information.

3. The endoscope device according to claim 2, wherein the moving direction determining section determines the moving direction of the focusing lens so that the observation depth is changed toward a direction by which the observation depth is moved from a focal position of an obtained image corresponding to a minimum contrast of the calculated contrasts to a focal position of an obtained image corresponding to a maximum contrast of the calculated contrasts.

4. The endoscope device according to claim 1, wherein the image capturing unit captures a near point image whose focal position is at a near point and a distant point image whose focal position is at a distant point,
wherein the moving direction determining section calculates a contrast F1 of the near point image and a contrast F2 of the distant point image, and determines that the observation depth is to be changed when the following conditional expression (1) is satisfied, $$(F1 \leq Th1) \cap (F2 \leq Th2) \tag{1}$$

wherein the near point threshold Th1 and the distant point threshold Th2 are predetermined so as to correspond to the position information of the focusing lens at the time of obtaining the near point image and the distant point image.

5. The endoscope device according to claim 4, wherein the moving direction determining section determines that the moving direction is a direction toward the near point when the following conditional expression (2) is satisfied, and that the moving direction is a direction toward the distant point when the following conditional expression (3) is satisfied, $$F1 > F2 \tag{2}$$

$$F1 \leq F2 \tag{3}$$

* * * * *